(12) United States Patent
Hubbell et al.

(10) Patent No.: US 6,331,422 B1
(45) Date of Patent: *Dec. 18, 2001

(54) ENZYME-MEDIATED MODIFICATION OF FIBRIN FOR TISSUE ENGINEERING

(75) Inventors: Jeffrey A. Hubbell, Zumiken; Jason Schense, Zürich, both of (CH)

(73) Assignee: California Institute of Technology, Pasadena, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/057,052

(22) Filed: Apr. 8, 1998

(51) Int. Cl.[7] .................................................. C12N 9/10

(52) U.S. Cl. ..................... 435/193; 424/423; 530/300; 530/350; 530/402; 514/2

(58) Field of Search ..................... 530/300, 350, 530/402; 435/183, 174; 514/2–21

(56) References Cited

U.S. PATENT DOCUMENTS

| | | | |
|---|---|---|---|
| 4,613,665 | 9/1986 | Larm | 536/20 |
| 4,810,784 | 3/1989 | Larm | 536/20 |
| 5,100,668 | 3/1992 | Edelman et al. | 424/422 |
| 5,504,001 | 4/1996 | Foster | 435/219 |
| 5,561,982 | 10/1996 | Marx | 424/450 |
| 5,693,341 | 12/1997 | Schroeder et al. | 424/488 |
| 5,958,874 * | 9/1999 | Clark | 514/2 |

FOREIGN PATENT DOCUMENTS

| | | |
|---|---|---|
| WO 89/0005 | 1/1989 | (WO) . |
| WO 90/05177 | 5/1990 | (WO) . |
| WO 92/22312 | 12/1992 | (WO) . |
| WO 95/05396 | 2/1995 | (WO) . |
| WO 95/23611 | 9/1995 | (WO) . |

OTHER PUBLICATIONS

*Development of Fibrin Derivatives for Controlled Release of Heparin–Binding Growth Factors*, Shelly E. Sakiyama–Elbert and Jeffrey A. Hubbell, University of Zurich, one page.
*Structure–Function Relationship of Basic Fibroblast Growth Factor: Site–Directed Mutagenesis of a Putative Heparin–Binding and Receptor–Binding Region*, M. Presta et al, Academic Press, Inc., 1992, Biochemical and Biophysical Research Communications, pp. 1098–1107.
*Role of Morphogenetic Proteins in Skeletal Tissue Engineering and Regeneration*, A. Hari Reddi, Nature Biotechnology, vol. 16, Mar. 1998, pp. 247–252.
*Transforming Growth Factor–β1 Is a Heparin–Binding Protein: Identification of Putative Heparin–Binding Regions and Isolation of Heparins with Varying Affinity for TGF–β1*, Journal of Cellualr Physiology 152:430–440, 1992.
*Defining the Interleukin–8–Binding Domain of Heparan Sulfate*, Dorothe Spillmann et al, The Journal of Biological Chemistry, vol. 273, No. 25, Jun. 1998, pp. 15487–15493.
*Neurotrophin–6 is a new member of the nerve growth factor family*, Rudolf Gotz et al, Nature, vol. 372, Nov. 17, 1994, pp. 266–269.
*Heparin Modulates the Interaction of VEGF 165 with Soluble and Cell Associated flk–1 Receptors*, Shoshana Tessler et al, The Journal of Biological Chemistry, vol. 269, No. 17, Apr. 29, 1994, pp. 12456–12461.
*Altered Expression of Epidermal Growth Factor receptor Ligands in Tumor Promoter–Treated Mouse Epidermis and In Primary Mouse Skin Tumors Induced by an Initiation–Promotion Protocol*, Kaoru Kiguchi et al, Molecular Carcinogenesis 22:73–83, 1998.
*Characterization of Cell–Associated and Soluble Forms of Connective Tissue Growth Factor (CTGF) Produced by Fibroblast Cells in Vitro*, Christy 1. Steffen et al, Growth Factors, vol. 15, pp. 199–213.
*Midkine, a Heparin–Binding Growth/Differentiation Factor, Exhibits Nerve Cell Adhesion and Guidance Activity for Neurite Outgrowth in Vitro*, Norio Kaneda et al, J. Biochem, vol. 119, 1996, pp. 1150–1156.
*Developmentally Regulated Neurite Outgrowth Response fro mDorsal Root Ganglion Neurons to Heparin–binding Growth–associated Molecule (HB–GAM) and the xpression of HB–GAM in the Targets of the Developing Dorsal Root ganglion Neurites*, Riitta Nolo et al, European Journal of Neuroscience, vol. 8, pp. 1658–1665, 1996.
*Controlled and modulated release of basic fibroblast growth factor*, Elazer R. Edelman et al, Biomaterials, vol. 12, Sep. 1991, pp. 619–626.
*Heparin–fibroblast growth factor—0fibrin comples: in vitro and in vivo applications to collagen–based materials*, Chantal DeBlois et al, Biomaterials, vol. 15, No. 9, 1994, pp. 665–672.

(List continued on next page.)

Primary Examiner—Leon B. Lankford, Jr.
(74) Attorney, Agent, or Firm—Holland & Knight LLP

(57) ABSTRACT

The invention provides fibrin-based, biocompatible materials useful in promoting cell growth, wound healing, and tissue regeneration. These materials are provided as part of several cell and tissue scaffolding structures that provide particular application for use in wound-healing and tissue regenerating. Methods for preparing these compositions and using them are also disclosed as part of the invention. A variety of peptides may be used in conjunction with the practice of the invention, in particular, the peptide IKVAV, and variants thereof. Generally, the compositions may be described as comprising a protein network (e.g., fibrin) and a peptide having an amino acid sequence that comprises a transglutaminase substrate domain (e.g., a factor XIIIa substrate domain) and a bioactive factor (e.g., a peptide or protein, such as a polypeptide growth factor), the peptide being covalently bound to the protein network. Other applications of the technology include their use on implantable devices (e.g., vascular graphs), tissue and cell scaffolding. Other applications include use in surgical adhesive or sealant, as well as in peripheral nerve regeneration and angiogenesis.

39 Claims, 5 Drawing Sheets

OTHER PUBLICATIONS

*Calcium Alginate Beads as a Slow–Release System for Delivering Angiogenic Molecules in Vivo and In Vitro*, Elizabeth C. Downs, et al, Journal of Cellular Physiology 152: 422–429, 1992.

*Nerve growth factor (NGF)–treated nitrocellulose enhances and directs the regeneration of adult rat dorsal root axons throught intraspinal neural tissue transplants*, John D. Houle and James E. Johnson, Neuroscience Letters, vol. 103, 1989, pp. 17–23.

*Sustained Release of Nerve Growth Factor from Biodegradable Polymer Microspheres*, Paul J. Camarata et al, Neurosurgery, vol. 30, No. 3, 1992, pp. 313–319.

*Controlled Release of nerve growth factor from a polymeric implant*, Elizabeth M. Powell et al, Brain Research, vol. 515, 1990, pp. 309–311.

*Microencapsulated nerve growth factor: effects on the forebrain neurons following devascularizing cortical lesions*, Dusica Maysinger et al, Neuroscience Letters, vol. 140, 1992, pp. 71–74.

*Collagen and heparin matrices for growth factor delivery*, J. A. Schroeder–Tefft et al, Journal of Controlled Release, vol. 49, 1997, pp. 291–298.

*Molecular Modeling of Protein–Glycosaminoglycan Interactions*, Alan D. Cardin et al, Arteriosclerosis, vol. 9: 21–32, 1989.

*Effects of Fibrinolysis on Neurite Growth From Dorsal Root Ganglia Cultured in Two– and Three–Dimensional Fibrin Gels*, Curtis B. Herbert et al, The Journal of Comparative Neurology, vol. 365: 380–391 (1996).

*Cross–Linking Exogenous Bifunctional Peptides into Fibrin Gels with Factor XIIIa*, Jason C. Schense and Jeffrey A. Hubbell, Bioconjugate Chemistry, vol. 10, No. 1, pp. 75–81, 1999.

*Purification and Initial Characterization of Rat B49 Glial Cell Line–Derived Neurotrphic Factor*, Leu–Fen H. Lin et al, Journal of Neurochemistry, 1994, pp. 758–768.

*The Interaction of the Transforming Growth Facotr–βs with Heparin/Heparan Sulfate is Isoform–specific*, Malcolm Lyon et al, The Journal of Biological Chemistry, vol. 272, No. 29, 1997, pp. 18000–18006.

*Analysis of affinity and structural selectivity in the binding of proteins to glycosaminoglycans: Development of a sensitive electrophoretic approach*, Matthias Lee et al, Biochemistry, vol. 88, pp. 2768–2772, 1991.

Besson, C. J. et al, Analytical BioChemistry, vol. 237, Article No. 0232, *Synthetic Peptide Substrates for a Conductimetric Assay of Pseudomonas aeruginosa Elastase*, 1996, pp. 216–223.

Coombs, Gary S. et al, Journal of Biological Chemistry, vol. 273, No. 8, *Directing Sequence–specific Proteolysis to New Targets*, Feb. 20, 1998, pp. 4323–4328.

Götz, Rudolf et al, Letter to Nature, vol. 372, *Neurotrophin–6 is a new member of the nerve growth factor family*, Nov. 17, 1994, pp. 266–269.

Hata, Akira et al, Journal of Biological Chemistry, vol. 268, No. 12, *Binding of Lipoprotein Lipase to Heparin*, Apr. 25, 1993, pp. 8447–8457.

Haugen, Patricia K. et al, Journal of Neuroscience, vol. 12(6), *Central and Peripheral Neurite Outgrowth Differs in Preference for Heparin–Binding versus Integrin–Binding Sequences*, Jun. 1992, pp. 2034–2042.

Kallapur, S. G. et al, Journal of Neuroscience Research, vol. 33, *The Neural Cell Adhesion Molecule (NCAM) Heparin Binding Domain Binds to Cell Surface Heparan Sulfate Proteoglycans*, 1992, pp. 538–548.

Kaneda, Norio et al, Journal of Biochemistry, vol. 119, *Midkine, a Heparin–Binding Growth/Differentiation Factor, Exhibits Nerve Cell Adhesion and Guidance Activity for Neurite Outgrowth in Vitro*, 1996, pp. 1150–1156.

Kiguchi, Kaoru et al, Molecular Cardinogenesis, vol. 22, *Altered Expression of Epidermal Growth factor Receptor Ligands in Tumor Promoter–Treated Mouse Epidermis and in Primary Mouse Skin Tumors Induced by an Initiation–Promotion Protocol*, 1998, pp. 73–83.

Kinosaki, Masahiko et al, Biochemical Biophysica Acta, vol. 1384, *Identification of heparin–binding stretches of a naturally occurring deleted variant of hepatocyte growth factor (dHGF)*, 1998, pp. 93–102.

McCaffrey, Timothy A. et al, Journal of Cellular Physiology, vol. 152, *Transforming Growth Factor–β1 Is a Heparin–Binding Protein: Identification of Putative Heparin–Binding Regions and Isolation of Heparins with varying Affinity for TGF–β1*, 1992, pp. 430–440.

Netzel–Arnett, Sarah et al, Journal of Biological Chemistry, vol. 266, No. 11, *Sequence Specificities of Human Fibroblast and Neutropil Collagenases*, Apr. 15, 1991, pp. 6747–6755.

Nolo, Riitta et al, European Journal of Neuroscience, vol. 8, *Developmentally Regulated Neurite Outgrowth Response from Dorsal root Ganglion Neurons to Heparin–binding Growth–associated Molecule (HB–GAM) and the expression of HB–GAM ion the Targents of the Developing Dorsal Root Ganglion Neurites*, 1996, pp. 1658–1665.

Presta, M. et al, Biochemical and Biophysical research Communications, vol. 185, No. 3, *Structure–Function Relationship of Basic Fibroblast Growth Factor: Site–Directed Mutagenesis of a Putative Heparin–Binding and Receptor–Binding Region*, 1992, pp. 1098–1107.

Massia, Stephen P. et al, The Journal of Cell Biology, vol. 114, No. 5, *An RGD Spacing of 440 nm is Sufficient for Integrin $Ol_v\beta_3$–mediated Fibroblast Spreading and 140 nm for Focal contact and Stress Fiber Formation*, Sep. 1991, pp. 1089–110.

Yamada, Kenneth M., The Journal of Biological Chemistry, vol. 266, No. 20, *Adhesive Recognition Sequences*, Jul. 15, 1991, pp. 12809–12812.

DiMilla, Paul A. et al, Biophysical Journal, vol. 60, *Mathematical model for the effects of adhesion and mechanics on cell migration speed*, Jul. 1991, pp. 15–37.

Tashiro, K. et al, Journal of Biological Chemistry, vol. 264, No. 27, *A Synthetic Peptide containing the IKVAV Sequence from the A Chain of Laminin Mediates Cell Attachment, Migration, and Neurite Outgrowth*, Sep. 25, 1989, pp. 16174–16182.

Martin, George R., Annual Review of Cellular Biology, vol. 3, *Laminin and Other Basement Membrane Components*, 1987, p. 57–85.

Edgar, David et al, The EMBO Journal, vol. 3, No. 7, *The heparin–binding domain of laminin is responsible for its effects on nuerite outgrowth and neuronal survival*, 1984, pp. 1463–1468.

Borrajo, Alison M. P. et al, Bioorganic and Medicinal Chemistry Letters, vol. 7, No. 9, *Derivatized Cyclodextrins as Peptidomimetics: Influence on Neurite Growth*, 1997, pp. 1185–1190.

Kallapur, S. G. et al, Journal of Neuroscience Research, vol. 33, *The Neural Cell Adhesion Molecule (NCAM) Heparin Binding Domain Binds to Cell Surface Heparan Sulfate Proteoglycans*, 1992, pp. 538–548.

Kaneda, Norio et al, Journal of Biochemistry, vol. 119, *Midkine, a Heparin–Binding Growth/Differentiation Factor, Exhibits Nerve Cell Adhesion and Guidance Activity for Neurite Outgrowth in Vitro*, 1996, pp. 1150–1156.

Rogers, Sherry L. et al, Journal of Neuroscience, vol. 5, No. 2, *Neuron–Specific Interactions with Two Neurite–Promoting Fragments of Fibronectin*, Feb. 1985, pp. 369–378.

Herbert, Curtis B. et al, Journal of comparative Neurology, vol. 365, *Effects of Fibrinolysis on Neurite Growth From Dorsal Root Ganglia cultured in Two– and Three–Dimensional Fibrin Gels*, 1996, pp. 380–391.

Herbert, Curtis B. et al, Journal Biomed Mater Res. 40, *Effects of fibrin micromorphology on neurite growth from dorsal root ganglia cultured in three–dimensional fibrin gels*, 1998, pp. 551–559.

Kleinman, Hynda K. et al, Vitamins and Hormones, vol. 47, *The Laminins: A Family of Basement Membrane Glycoproteins Important in Cell Differentiation and Tumor Metastases*, 1993, pp. 161–186.

Zucker, Marjorie B. et al, Proceedings for the Society of Experimental biology and Medicine, vol. 198, *Platelet Factor 4: Production, Structure, and Physiologic and Immunologic Action*, 1991, pp. 693–702.

Smith, Matthew M. et al, Journal of Biological Chemistry, vol. 270, No. 12, *Rapid Identification of Highly Active and Selective Substrates for Stromelysin and Matrilysis Using Bacteriophage Peptide Display Libraries*, Mar. 24, 1995, pp. 6440–6449.

Spillman, Dorothe et al, Journal of Biological Chemistry, vol. 273, No. 25, *Defining the Interleukin–8–Binding Domain of Heparan Sulfate*, Jun. 19, 1998, pp. 15487–15493.

Steffen, Christy L., et al, Growth Factors, vol. 15, *Characterization of Cell–Associated and Soluble Forms of Connective Tissue Growth Factor (CTFG) Produced by Fibroblast Cells in Vitro*, 1998, pp. 199–213.

Studier, F. William et al, Methods in Enzymology, vol. 185, *Use of T7 RNA Polymers to Direct expression of Cloned Genes*, 1990, p. 60–89.

Takagi, Takashi et al, Biochemistry, vol. 14, No. 23, *Amino Acid Sequence Studies on the Chain of Human Fibrinogen. Location of Four Plasmin Attack Points and a Covalent cross–linking Site*, 1975, pp. 5149–5156.

Tessler, Shoshana et al, Journal of Biological Chemistry, vol. 269, No. 17, *Heparin Modulates the Interaction of $VEGF_{165}$ with Soluble and Cell Associated flk–1 Receptors*, Apr. 29, 1994, pp. 12456–12461.

Tyler–Cross, Ruth et al, Protein Science, vol. 3, *Heparin binding domain peptides of antithrombin III: Analysis by isothermal titration calorimetry and circular dichroism spectroscopy*, 1994, pp. 620–627.

Yanish–Perron, Celeste et al, Gene, vol. 33, *Improved M13 phage cloning vectors and host strains: nucleotide sequences of the M13mp18 and pUC19 vectors*, 1985, pp. 103–119.

Dinbergs, Iveta D. et al, Journal of Biological Chemistry, vol. 271, No. 47, *Cellular Response to Transforming Growth factor–$\beta 1$ and Basic Fibroblast Growth factor Depends on release Kinetics and Extracellular Matrix Interactions*, Nov. 22, 1996, pp. 29822–29829.

Edelman, Elazer R. et al, Biomaterials, vol. 12, *Controlled and modulated release of basic fibroblast growth factor*, Sep. 1991, pp. 619–626.

Edelman, Elazer R. et al, Proc. Natl. Acad. Sci USA, vol. 90, *Perivascular and intravenous administration of basic fibroblast growth factor: Vascular and solid organ deposition*, Feb. 1993, pp. 1513–1517.

Edelman, Elazer R. et al, The American Society for Clinical Investigation, Inc., vol. 89, *Basic Fibroblast Growth Factor Enhances the Coupling of Intimal Hyperplasia and Proliferation of Vasa Vasorum in Injured Rat Arteries*, Feb. 1992, pp. 465–473.

Harada, Kazumasa et al, The American Society for Clinical Investigation, Inc., vol. 94, *Basic Fibroblast Growth Factor Improves Myocardial Function in chronically Ischemic Porcine Hearts*, Aug. 1994, pp. 623–630.

Lopez, John J. et al, Drug Metabolism and Disposition, vol. 24, No. 8, *Short Communication, Local Perivascular Administration of Basic Fibroblast Growth Factor: Drug Delivery and Toxicological Evaluation*, Dec. 1995, pp. 922–924.

Lopez, John J. et al, The Journal of Pharmacology and Experimental Therapeutics, vol. 282, No. 1, *Basic Fibroblast Growth Factor in a Porcine Model of Chronic Myocardial Ischemia: A Comparison of Angiographic, Echocardiographic and Coronary Flow Parameters*, Nov. 1996, pp. 385–390.

Sellke, Frank W. et al, *Basic FGF enhances endothelium–dependent relaxation of the collateral–perfused coronary microcirculation*, 1994, pp. H1303–1311.

* cited by examiner

SEQUENCE LISTING (1) GENERAL INFORMATION:

(iii) NUMBER OF SEQUENCES: 20

(2) INFORMATION FOR SEQ ID NO:1:

(i) SEQUENCE CHARACTERISTICS:
        (A) LENGTH: 5 amino acids
        (B) TYPE: amino acid
        (C) STRANDEDNESS:
        (D) TOPOLOGY: linear (xi) SEQUENCE DESCRIPTION: SEQ ID NO:1:

Tyr Ile Gly Ser Arg
1               5

(2) INFORMATION FOR SEQ ID NO:2:

(i) SEQUENCE CHARACTERISTICS:
        (A) LENGTH: 5 amino acids
        (B) TYPE: amino acid
        (C) STRANDEDNESS:
        (D) TOPOLOGY: linear (xi) SEQUENCE DESCRIPTION: SEQ ID NO:2:

Leu Arg Gly Asp Asn
1               5

(2) INFORMATION FOR SEQ ID NO:3:

(i) SEQUENCE CHARACTERISTICS:
        (A) LENGTH: 5 amino acids
        (B) TYPE: amino acid
        (C) STRANDEDNESS:
        (D) TOPOLOGY: linear (xi) SEQUENCE DESCRIPTION: SEQ ID NO:3:

Pro Asp Gly Ser Arg
1               5

(2) INFORMATION FOR SEQ ID NO:4:

(i) SEQUENCE CHARACTERISTICS:
        (A) LENGTH: 5 amino acids
        (B) TYPE: amino acid
        (C) STRANDEDNESS:
        (D) TOPOLOGY: linear (xi) SEQUENCE DESCRIPTION: SEQ ID NO:4:

Ile Lys Val Ala Val
1               5

(2) INFORMATION FOR SEQ ID NO:5:

(i) SEQUENCE CHARACTERISTICS:
        (A) LENGTH: 10 amino acids
        (B) TYPE: amino acid
        (C) STRANDEDNESS:
        (D) TOPOLOGY: linear (xi) SEQUENCE DESCRIPTION: SEQ ID NO:5:

Arg Asn Ile Ala Glu Ile Ile Lys Asp Ile
1               5                   10

(2) INFORMATION FOR SEQ ID NO:6:

(i) SEQUENCE CHARACTERISTICS:
    (A) LENGTH: 4 amino acids
    (B) TYPE: amino acid
    (C) STRANDEDNESS:
    (D) TOPOLOGY: linear (xi) SEQUENCE DESCRIPTION: SEQ ID NO:6:

Asp Gly Glu Ala
1

(2) INFORMATION FOR SEQ ID NO:7:

(i) SEQUENCE CHARACTERISTICS:
        (A) LENGTH: 6 amino acids
        (B) TYPE: amino acid
        (C) STRANDEDNESS:
        (D) TOPOLOGY: linear (xi) SEQUENCE DESCRIPTION: SEQ ID NO:7:

Pro Arg Arg Ala Arg Val
1               5

(2) INFORMATION FOR SEQ ID NO:8:

(i) SEQUENCE CHARACTERISTICS:
        (A) LENGTH: 16 amino acids
        (B) TYPE: amino acid
        (C) STRANDEDNESS:
        (D) TOPOLOGY: linear (xi) SEQUENCE DESCRIPTION: SEQ ID NO:8:

Tyr Arg Gly Asp Thr Ile Gly Glu Gly Gln Gln His His Leu Gly Gly
1               5                   10                  15

(2) INFORMATION FOR SEQ ID NO:9:

(i) SEQUENCE CHARACTERISTICS:
        (A) LENGTH: 9 amino acids
        (B) TYPE: amino acid
        (C) STRANDEDNESS:
        (D) TOPOLOGY: linear (xi) SEQUENCE DESCRIPTION: SEQ ID NO:9:

Leu Arg Gly Asp Gly Ala Lys Asp Val
1               5

(2) INFORMATION FOR SEQ ID NO:10:

(i) SEQUENCE CHARACTERISTICS:
        (A) LENGTH: 9 amino acids
        (B) TYPE: amino acid
        (C) STRANDEDNESS:
        (D) TOPOLOGY: linear (xi) SEQUENCE DESCRIPTION: SEQ ID NO:10:

Leu Arg Gly Asp Lys Lys Lys Lys Gly
1               5

(2) INFORMATION FOR SEQ ID NO:11:

(i) SEQUENCE CHARACTERISTICS:
        (A) LENGTH: 12 amino acids
        (B) TYPE: amino acid
        (C) STRANDEDNESS:
        (D) TOPOLOGY: linear (xi) SEQUENCE DESCRIPTION: SEQ ID NO:11:

```
Leu Asn Gln Glu Gln Val Ser Pro Leu Arg Gly Asp
1               5                   10
```

(2) INFORMATION FOR SEQ ID NO:12:

(i) SEQUENCE CHARACTERISTICS:
        (A) LENGTH: 16 amino acids
        (B) TYPE: amino acid
        (C) STRANDEDNESS:
        (D) TOPOLOGY: linear (xi) SEQUENCE DESCRIPTION: SEQ ID NO:12:

```
Tyr Arg Gly Asp Thr Ile Gly Glu Gly Gln Gln His His Leu Gly Gly
1               5                   10                  15
```

(2) INFORMATION FOR SEQ ID NO:13:

(i) SEQUENCE CHARACTERISTICS:
        (A) LENGTH: 5 amino acids
        (B) TYPE: amino acid
        (C) STRANDEDNESS:
        (D) TOPOLOGY: linear (xi) SEQUENCE DESCRIPTION: SEQ ID NO:13:

```
Gly Ala Lys Asp Val
1               5
```

(2) INFORMATION FOR SEQ ID NO:14:

(i) SEQUENCE CHARACTERISTICS:
        (A) LENGTH: 4 amino acids
        (B) TYPE: amino acid
        (C) STRANDEDNESS:
        (D) TOPOLOGY: linear (xi) SEQUENCE DESCRIPTION: SEQ ID NO:14:

```
Lys Lys Lys Lys
1
```

(2) INFORMATION FOR SEQ ID NO:15:

(i) SEQUENCE CHARACTERISTICS:
        (A) LENGTH: 8 amino acids
        (B) TYPE: amino acid
        (C) STRANDEDNESS:
        (D) TOPOLOGY: linear (xi) SEQUENCE DESCRIPTION: SEQ ID NO:15:

```
Asn Gln Glu Gln Val Ser Pro Leu
1               5
```

(2) INFORMATION FOR SEQ ID NO:16:

(i) SEQUENCE CHARACTERISTICS:
        (A) LENGTH: 15 amino acids
        (B) TYPE: amino acid
        (C) STRANDEDNESS:
        (D) TOPOLOGY: linear (xi) SEQUENCE DESCRIPTION: SEQ ID NO:16:

```
Leu Asn Gln Glu Gln Val Ser Pro Leu Gly Tyr Ile Gly Ser Arg
1               5                   10                  15
```

(2) INFORMATION FOR SEQ ID NO:17:

(i) SEQUENCE CHARACTERISTICS:
        (A) LENGTH: 15 amino acids
        (B) TYPE: amino acid

```
            (C) STRANDEDNESS:
            (D) TOPOLOGY: linear (xi) SEQUENCE DESCRIPTION: SEQ ID NO:17:

Leu Asn Gln Glu Gln Val Ser Pro Leu Asp Asp Gly Glu Ala Gly
1               5                   10                  15

(2) INFORMATION FOR SEQ ID NO:18:

(i) SEQUENCE CHARACTERISTICS:
            (A) LENGTH: 16 amino acids
            (B) TYPE: amino acid
            (C) STRANDEDNESS:
            (D) TOPOLOGY: linear (xi) SEQUENCE DESCRIPTION: SEQ ID NO:18:

Leu Asn Gln Glu Gln Val Ser Pro Leu Arg Ala His Ala Val Ser Glu
1               5                   10                  15

(2) INFORMATION FOR SEQ ID NO:19:

(i) SEQUENCE CHARACTERISTICS:
            (A) LENGTH: 17 amino acids
            (B) TYPE: amino acid
            (C) STRANDEDNESS:
            (D) TOPOLOGY: linear (xi) SEQUENCE DESCRIPTION: SEQ ID NO:19:

Leu Asn Gln Glu Gln Val Ser Pro Arg Asp Ile Lys Val Ala Val Asp
1               5                   10                  15

Gly (2) INFORMATION FOR SEQ ID NO:20:

(i) SEQUENCE CHARACTERISTICS:
            (A) LENGTH: 19 amino acids
            (B) TYPE: amino acid
            (C) STRANDEDNESS:
            (D) TOPOLOGY: linear (xi) SEQUENCE DESCRIPTION: SEQ ID NO:20:

Leu Asn Gln Glu Gln Val Ser Pro Arg Asn Ile Ala Glu Ile Ile Lys
1               5                   10                  15

Asp Ile Arg
```

ENZYME-MEDIATED MODIFICATION OF FIBRIN FOR TISSUE ENGINEERING

CROSS-REFERENCE TO RELATED APPLICATIONS

This application is continuation of International Application No. PCT/US98/06617, filed Apr. 2, 1998, which claims priority to U.S. Provisional application Ser. No. 60/042,143 filed Apr. 3, 1997.

The United States Government has certain rights in this invention pursuant to Grant No: USPHS HD 31462-01A1, awarded by the National Institute of Health.

BACKGROUND OF THE RELATED ART

Fibrin is a natural gel with several biomedical applications. Fibrin gel has been used as a sealant because of its ability to bind to many tissues and its natural role in wound healing. Some specific applications include use as a sealant for vascular graft attachment, heart valve attachment, bone positioning in fractures and tendon repair (Sierra, D. H., *Journal of Biomaterials Applications*, 7:309–352,1993). Additionally, these gels have been used as drug delivery devices, and for neuronal regeneration (Williams, et al., *Journal of Comparative Neurobiology*, 264:284–290, 1987).

The process by which fibrinogen is polymerized into fibrin has also been characterized. Initially, a protease cleaves the dimeric fibrinogen molecule at the two symmetric sites. There are several possible proteases that can cleave fibrinogen, including thrombin, reptilase, and protease III, and each one severs the protein at a different site (Francis, et al., *Blood Cells*, 19:291–307, 1993). Each of these cleavage sites have been located (FIG. 1). Once the fibrinogen is cleaved, a self-polymerization step occurs in which the fibrinogen monomers come together and form a non-covalently crosslinked polymer gel (Sierra, 1993). A schematic representation of the fibrin polymer is shown in FIG. 2. This self-assembly happens because binding sites become exposed after protease cleavage occurs. Once they are exposed, these binding sites in the center of the molecule can bind to other sites on the fibrinogen chains, these sites being present at the ends of the peptide chains (Stryer, L. *In Biochemistry*, W. H. Freeman & Company, N.Y., 1975). In this manner, a polymer network is formed. Factor XIIIa, a transglutaminase activated from factor XIII by thrombin proteolysis, may then covalently cross-link the polymer network. Other transglutaminases exist and may also be involved in covalent crosslinking and grafting to the fibrin network.

Once a crosslinked fibrin gel is formed, the subsequent degradation is tightly controlled. One of the key molecules in controlling the degradation of fibrin is α2-plasmin inhibitor (Aoki, N., *Progress in Cardiovascular Disease*, 21:267–286, 1979). This molecule acts by crosslinking to the α chain of fibrin through the action of factor XIIIa (Sakata, et al., *Journal of Clinical Investigation*, 65:290–297, 1980). By attaching itself to the gel, a high concentration of inhibitor can be localized to the gel. The inhibitor then acts by preventing the binding of plasminogen to fibrin (Aoki, et al., *Thrombosis and Haemostasis*, 39:22–31, 1978) and inactivating plasmin (Aoki, 1979). The α-2 plasmin inhibitor contains a glutamine substrate. The exact sequence has been identified as NQEQVSPL (SEQ ID NO: 15), with the first glutamine being the active amino acid for crosslinking.

The components required for making fibrin gels can be obtained in two ways. One method is to cryoprecipitate the fibrinogen from plasma. In this process, factor XIII precipitates with the fibrinogen, so it is already present. The proteases are purified from plasma using similar methods. Another technique is to make recombinant forms of these proteins either in culture or with transgene animals. The advantage of this is that the purity is much higher, and the concentrations of each of these components can be controlled.

Cells interact with their environment through protein-protein, protein-oligosaccharide and protein-polysaccharide interactions at the cell surface. Extracellular matrix proteins provide a host of bioactive signals to the cell. This dense network is required to support the cells, and many proteins in the matrix have been shown to control cell adhesion, spreading, migration and differentiation (Carey, *Annual Review of Physiology*, 53:161–177, 1991). Some of the specific proteins that have shown to be particularly active include laminin, vitronectin, fibronectin, fibrin, fibrinogen and collagen (Lander, *Journal of Trends in Neurological Science*, 12:189–195, 1989). Many studies of laminin have been conducted, and it has been shown that laminin plays a vital role in the development and regeneration of nerves in vivo and nerve cells in vitro (Williams, *Neurochemical Research*, 12:851–869, 1987; Williams, et al., 1993), as well as in angiogenesis.

Some of the specific sequences that directly interact with cellular receptors and cause either adhesion, spreading or signal transduction have been identified. This means that the short active peptide sequences can be used instead of the entire protein for both in vivo and in vitro experiments. Laminin, a large multidomain protein (Martin, *Annual Review of Cellular Biology*, 3:57–85, 1987), has been shown to consist of three chains with several receptor-binding domains. These receptor-binding domains include the YIGSR (SEQ ID NO: 1) sequence of the laminin B1 chain (Graf, et al., *Cell*, 48:989–996, 1987; Kleinman, et al., *Archives of Biochemistry and Biophysics*, 272:39–45, 1989; and Massia, et al., *J. of Biol. Chem.*, 268:8053–8059, 1993), LRGDN (SEQ ID NO: 2) of the laminin A chain (Ignatius, et al., *J. of Cell Biology*, 111:709–720, 1990) and PDGSR (SEQ ID NO: 3) of the laminin B1 chain (Kleinman, et al., 1989). Several other recognition sequences for neuronal cells have also been identified. These include IKVAV (SEQ ID NO: 4) of the laminin A chain (Tashiro, et al., *J. of Biol. Chem.*, 264:16174–16182, 1989) and the sequence RNIAEI-IKDI (SEQ ID NO: 5) of the laminin B2 chain (Liesi, et al., *FEBS Letters*, 244:141–148, 1989). The receptors that bind to these specific sequences have also often been identified. A subset of cellular receptors that has shown to be responsible for much of the binding is the integrin superfamily (Rouslahti, E., *J. of Clin. Investigation*, 87:1–5, 1991). Integrins are protein heterodimers that consist of α and β subunits. Previous work has shown that the tripeptide RGD binds to several $\beta_1$ and $\beta_3$ integrins (Hynes, R. O., *Cell*, 69:1–25, 1992; Yamada, K. M., *J. of Biol. Chem.*, 266:12809–12812, 1991), IKVAV(SEQ ID NO: 4) binds to a 110 kDa receptor (Tashiro, et al., *J. of BioL Chem.*, 264:16174–16182, 1989; Luckenbill-Edds, et al., *Cell Tissue Research*, 279:371–377, 1995), YIGSR (SEQ ID NO: 1) binds to a 67 kDa receptor (Graf, et al., 1987) and DGEA (SEQ ID NO: 6), a collagen sequence, binds to the $\alpha_2,\beta_1$ integrin (Zutter & Santaro, *Amer. J. of Pathology*, 137:113–120, 1990). The receptor for the RNIAEIIKDI (SEQ ID NO: 5) sequence has not been reported.

Work has been done in crosslinking bioactive peptides to large carrier molecules and incorporating them within fibrin gels. By attaching the peptides to the large carrier polymers, the rate of diffusion out of the fibrin gel will be slowed down. In one series of experiments, polyacrylic acid was used as the carrier polymer and various sequences from laminin were covalently bound to them to confer neuroactivity (Herbert, C. in *Chemical Engineering* 146) to the gel. The stability of such a system was poor due to a lack of covalent or high affinity binding between the fibrin and the bioactive molecule.

Very little work has been done in incorporating peptide sequences and other bioactive factors into fibrin gels and even less has been done in covalently binding peptides directly to fibrin. However, a significant amount of energy has been spent on determining which proteins bind to fibrin via enzymatic activity and often determining the exact sequence which binds as well. The sequence for fibrin γ-chain crosslinking has been determined and the exact site has been located as well (Doolittle, et al., *Biochem. & Biophys. Res. Comm.,* 44:94–100, 1971). Factor XIIIa has also been shown to crosslink fibronectin to fibronectin (Barry & Mosher, *J. of Biol. Chem.,* 264:4179–4185, 1989), as well as fibronectin to fibrin itself (Okada, et al., *J. of Biol. Chem.,* 260:1811–1820, 1985). This enzyme also crosslinks von Willebrand factor (Hada, et al., *Blood,* 68:95–101, 1986), as well as α-2 plasmin inhibitor (Tamaki & Aoki, *J. of Biol. Chem.,* 257:14767–14772, 1982), to fibrin. The specific sequence that binds from α-2 plasmin inhibitor has been isolated (Ichinose, et al., *FEBS Letters,* 153:369–371, 1983) in addition to the number of possible binding sites on the fibrinogen molecule (Sobel & Gawinowicz, *J. of Biol. Chem.,* 271:19288–19297, 1996) for α-2 plasmin inhibitor. Thus, many substrates for factor XIII exist, and a number of these have been identified in detail.

SUMMARY OF THE INVENTION

The present invention in a general and overall sense, provides unique fusion proteins and other factors, either synthetically or recombinantly, that contain both a transglutaminase domain, such as a Factor XIII, a substrate domain and a bioactive factor, these peptides being covalently attached to a fibrin substrate having a three-dimensional structure capable of supporting cell growth.

In some embodiments of the present invention, bioactive properties found in extracellular matrix proteins and surface proteins are confined to a structurally favorable matrix that can readily be remodeled by cell-associated proteolytic activity. In some embodiments, the fibrin is gel matrix. A bioactive means is also included to facilitate the incorporation of an exogenous signal into the substrate. In addition to retaining the bioactivity of the exogenous signal molecule, the overall structural characteristics of the fibrin gel is maintained.

The invention in another aspect provides for a fibrin matrix comprising short peptides covalently crosslinked thereto, as well as bioactive factors. The fibrin matrix may be further defined as a fibrin gel. The matrix chosen is fibrin, since it provides a suitable three dimensional structure for tissue growth and is the native matrix for tissue healing. It is anticipated that other, fibrin-like matrices may also be similarly prepared. The crosslinking was accomplished enzymatically by using the native Factor XIII to attach the exogenous factors to the gels. In order to do this, a sequence that mimics a crosslinking site was incorporated into the peptide so that the enzyme recognized and crosslinked it into the matrix. Novel activity will be conferred to these fibrin gels by adding a peptide sequence, or other bioactive factor, which is attached to the crosslinking sequence. These materials may be useful in the promotion of healing and tissue regeneration, in the creation of neurovascular beds for cell transplantation and in numerous other aspects of tissue engineering. Hence, the invention in yet other aspects provides compositions created and adapted for these specific uses.

The following sequences are referenced throughout the Specification:

| SEQ ID NO: | DESCRIPTION |
|---|---|
| SEQ ID NO: 1 | YIGSR - Peptide that binds to a 67 kDa receptor |
| SEQ ID NO: 2 | LRGDN - Peptide of the laminin A chain |
| SEQ ID NO: 3 | PDGSR - Peptide of the laminin B1 chain |
| SEQ ID NO: 4 | IKVAV - Peptide that binds to a 110 kDa receptor |
| SEQ ID NO: 5 | RNIAEIIKDI - Peptide of the laminin B2 chain |
| SEQ ID NO: 6 | DGEA - A collagen peptide that binds to the $\alpha_2$, $\beta_1$ integrin |
| SEQ ID NO: 7 | PRRARV - A sequence from fibronectin is also a heparin sulfate binding sequence |
| SEQ ID NO: 8 | YRGDTIGEGQQHHLGG - A peptide with glutamine at the transglutaminase coupling site, an active RGD sequence and a dansylated amino acid, mimics the crosslinking site in the γ chain of fibrinogen |
| SEQ ID NO: 9 | LRGDGAKDV - A peptide that mimics the lysine coupling site in the δ chain of fibrinogen with an active RGD sequence and a dansylated leucine added |
| SEQ ID NO: 10 | LRGKKKKG - A peptide with a polylysine at a random coupling site attached to an active RGD and a dansylated lecine |
| SEQ ID NO: 11 | LNQEQVSPLRGD - A peptide that mimics the crosslinking site in α2-plasmin inhibitor with an active RGD added to the carboxy terminus and a dansylated leucine to the amino terminus |
| SEQ ID NO: 12 | YRGDTIGEGQQHHLGG - A peptide with glutamine at the transglutaminase coupling site in the chain of fibrinogen |
| SEQ ID NO: 13 | GAKDV - A peptide that mimics the lysine coupling site in the chain of fibrinogen |
| SEQ ID NO: 14 | KKKK - A peptide with a polylysine at a random coupling site |
| SEQ ID NO: 15 | NQEQVSPL - A peptide that mimics the crosslinking site in 2- plasmin inhibitor |
| SEQ ID NO: 16 | LNQEQVSPLGYIGSR - A peptide that mimics the crosslinking site in α2-plasmin inhibitor with an active YIGSR added to the carboxy terminus and a dansylated leucine to the amino terminus |
| SEQ ID NO: 17 | LNQEQVSPLDDGEAG - A peptide that mimics the crosslinking site in α2-plasmin inhibitor with an active DGEA |
| SEQ ID NO: 18 | LNQEQVSPLRAHAVSE - A peptide that mimics the crosslinking site in α2-plasmin inhibitor with an active HAV added to the carboxy terminus and a dansylated leucine to the amino terminus |
| SBQ ID NO: 19 | LNQEQVSPRDIKVAVDG - A peptide that mimics the crosslinking site in α2-plasmin inhibitor with an active IKVAV added to the carboxy terminus and a dansylated leucine to the amino terminus |
| SEQ ID NO: 20 | LNQEQVSPRNIAEIIKDIR - A peptide that mimics the crosslinking site in α2-plasmin inhibitor with an active RNIAEIIKDI added to the carboxy terminus and a daysylated leucine to the amino terminus |

In one aspect, the invention provides a composition that comprises a protein network and a peptide having an amino acid sequence that comprises a transglutaminase substrate domain and a bioactive factor (e.g., peptide, protein, or fragment thereof) is provided. The peptide is covalently or at least substantially covalently bound to the protein network. In particular embodiments, the protein network is fibrin or a fibrin-like molecule. In other particular embodiments, the transglutaminase substrate domain is a factor XIIIa substrate domain. This factor XIIIa substrate domain may be further defined as comprising an amino acid sequence SEQ ID NO: 12, SEQ ID NO: 13, SEQ ID NO: 14, SEQ ID NO: 15, a fragment thereof, a combination thereof, or a bioactive fragment of said combination. Some embodiments may be defined as comprising a bioactive factor that comprises an amino acid sequence of SEQ ID NO: 1, SEQ ID NO: 2, SEQ ID NO: 3, SEQ ID NO: 4, SEQ ID NO: 5, SEQ ID NO: 6, a fragment thereof, a combination thereof, or a bioactive fragment of said combination.

In another aspect, the invention provides an implantable device having at least one surface or portion of at least one surface that comprises the composition of any one of the above compositions described herein. By way of example, the implantable device may be fashioned as an artificial joint device, such as a knee replacement. The invention may also take the form of a porous vascular graft, wherein at least one region or a portion of at least one region of the porous vascular graft comprises a porous wall that includes the composition of the protein network and covalently attached peptide/protein described herein. The invention as a device may be further defined in other embodiments as a scaffold for skin, bone, nerve or other cell growth, comprising a surface that includes at least one region or area that comprises the composition of the protein matrix and covalently attached peptide described herein.

In yet another aspect, the invention provides for a surgical sealant or adhesive comprising a surface that includes the composition of the peptide matrix and covalently attached peptide on at least one region of the surface.

The invention further provides methods for promoting cell growth or tissue regeneration. This method comprises in some embodiments, covalently attaching or producing a covalently attached bioactive complex molecule comprising a bioactive factor and a transglutaminase substrate, covalently coupling the bioactive complex molecule to a peptide network capable of having covalently attached thereto the bioactive factor or a fragment thereof, to provide a treated peptide substrate; and exposing said treated peptide substrate to a composition comprising cells or tissue to promote cell growth or tissue regeneration. This method may be used in conjunction with a variety of different cell types and tissue types. By way of example, such cell types include nerve cells, skin cells, and bone cells. The peptide network may be further defined as a protein network, such as a fibrin network. The transglutaminase substrate may be further defined as a factor XIIIa substrate, while the transglutaminase may be further defined as factor XIIIa. The factor XIIIa substrate may be further defined as having an amino acid sequence of SEQ ID NO. 12, SEQ ID NO. 13, SEQ ID NO. 14, SEQ ID NO. 15, a fragment thereof, a combination thereof, or a bioactive peptide fragment of said composition. The peptide may, in some embodiments, be further defined as comprising an amino acid sequence of SEQ ID NO. 1, SEQ ID NO. 2, SEQ ID NO. 3, SEQ ID NO. 4, SEQ ID NO. 5, SEQ ID NO. 6, a fragment thereof, a combination thereof or a bioactive peptide fragment thereof.

The invention in yet another aspect may be defined as a biosupportive matrix material. This material in some aspects, comprises a peptide network and a bioactive factor, wherein said bioactive factor is covalently attached to the peptide substrate. This peptide substrate may be further defined as a protein network. The bioactive factor is covalently attached to the substrate through a transglutaminase or a similar enzyme. The peptide that may be used in conjunction with the invention may comprise any variety of peptides capable of being covalently attached to the fibrin substrate or biosupportive matrix as described herein. In some embodiments, the peptide may be further defined as comprising an amino acid sequence of SEQ ID NO. 1, SEQ ID NO. 4, SEQ ID NO. 5, SEQ ID NO. 10, a fragment thereof, a combination thereof, or a bioactive fragment thereof.

In particular embodiments of the matrix compositions, the calculated moles of peptide that is to be included may be defined or described for those devices/surfaces that include them, as virtually any amount of peptide that falls within a physiologically relevant concentration of the particular peptide/protein selected. For a standard gel, 1 mg of fibrinogen would typically be included. Hence the concentration of fibrinogen in this standard gel may be described as about $3 \times 10^{-6}$ mM. Using this figure as a benchmark in one example, the ratio of the amount of peptide to fibrinogen could be expressed as about $3 \times 10^{-6}$ mM to about $24 \times 10^{-6}$ mM.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE PREFERRED EMBODIMENTS

Figure 1:
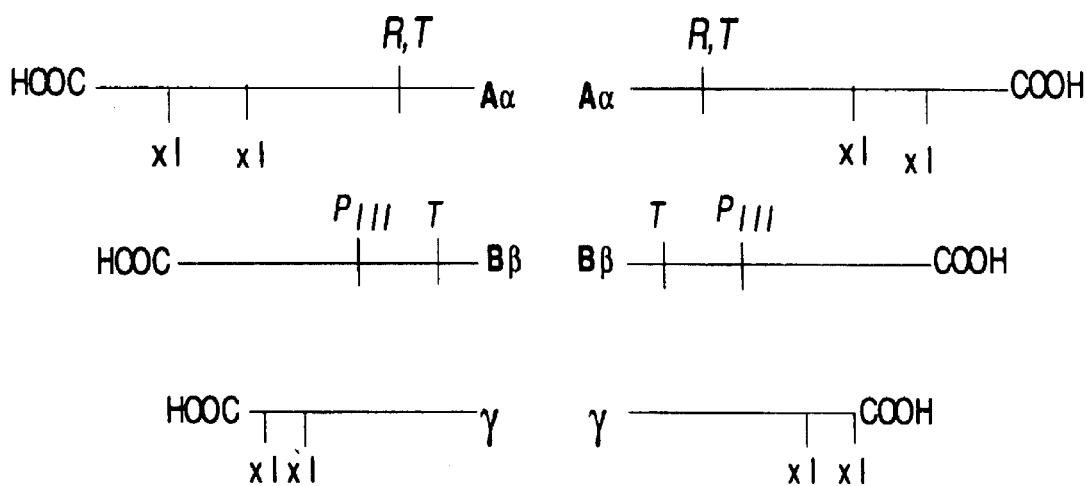
FIG. 1. The homodimeric structure of fibrinogen has been elucidated. Each symmetric half of fibrinogen is itself a heterodimers of the three chains Am, BE and y. Here, the cleavage sites of the major proteases have been marked (R is for reptilase, T is for thrombin and P III is for protease III). Additionally, some of the sites where cross linking can occur have been marked as xl.
Figure 2:
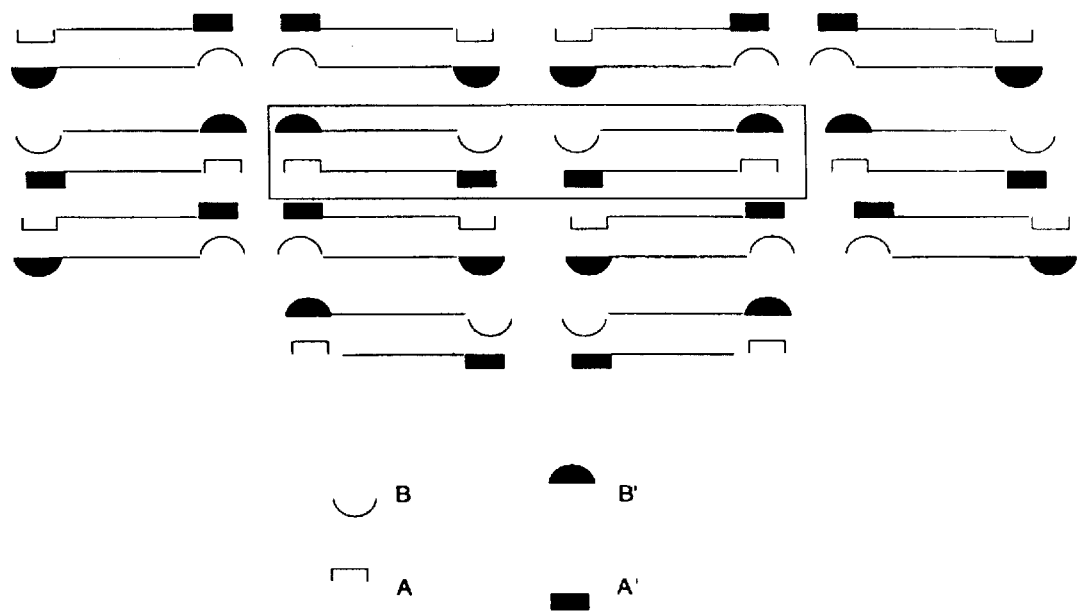
FIG. 2. A schematic representation of fibrinogen is given. The polymer is held together by the binding of sites B to B' and A to A'. A' and B only become available for binding after cleavage by a protease. The polymerization reaction is self-activated. A single monomer unit is boxed in the center.

Following long-standing patent law convention, the terms "a" and "an" mean "one or more" when used in this application, including the claims.

Using standard solid phase peptide synthesis, peptides with sequences that combine crosslinking sites from fibrinogen or another protein that crosslinks to fibrin gels, and active sequences, such as RGD or IKVAV (SEQ ID NO: 4) were created. A dansyl group was added to the primary amine of the peptide so that the molecule could be detected when in the presence of other proteins. The peptides were syringe filtered and freeze dried to purify.

Fibrin gels were created using thrombin as the enzyme. Thrombin, calcium, dansylated peptide and Tris Buffered Saline (pH 7) were mixed to achieve the proper concentration of all components. Dialyzed fibrinogen that contains residual factor XIII was added and the gels were polymerized in an incubator. The final gel concentrations for each component were 4 mg/ml of fibrinogen, 2.5 mM $CA^{++}$, 2 NIH units/ml of thrombin and various amounts of peptide. The gels were then covered with Phosphate Buffered Saline, and the buffer was changed until all the free peptide had diffused from the gel. The gels were then degraded with the minimal amount of plasmin necessary to achieve complete degradation.

One method used to analyze the results is as follows. The resulting products were run out on a gel permeation chromatography column and analyzed using a photodiode array detector. With this detector, we can collect and analyze data at many wavelengths at the same time. Chromatograms of each run were made at 280 nm (this signal is proportional to the total protein present. 205 rim can be used as well). The results were compared to a standard curve created from degraded fibrinogen and the total fibrin concentration was calculated. A fluorescence detector was used to measure the presence of peptide. The sample was excited at a wavelength of 330 nm and the emitted energy at 530 rim was measured (this is proportional to the total amount of dansyl groups present). These results were compared to standards curves created for each peptide and the ratio of peptide molecules to fibrin molecules in the gel was determined for a series of peptide concentrations. Furthermore, since a size exclusion column was used, it could be determined if the size of the peptide fragments in the gel were larger, smaller or the same as that of free peptide. If they are larger, then this is evidence that the peptide is directly bound to some fragment of gel and a covalent bond has actually been formed.

A second method used to analyze the substrates of the present invention for amount of peptide was as follows. Each gel was washed several times, and the amount of peptide present in each wash was measured on a spectofluorimeter. The gels were then degraded with plasmin and then the amount of fluor present was measured. The percent of fluor in the gel compared to the washes was calculated and since the initial peptide mass is known, the mass of peptide in the gels was calculated from this. When the fibrinogen was dissolved, the total mass dissolved was known and this was used to determine the mass of fibrinogen present in the gel. A different concentration of peptide was used in each series of studies and curves relating the total peptide incorporated with the initial peptide used were made.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Peptide Bound Per Molecule of Fibrinogen to Fibrin Gels

Figure 3:
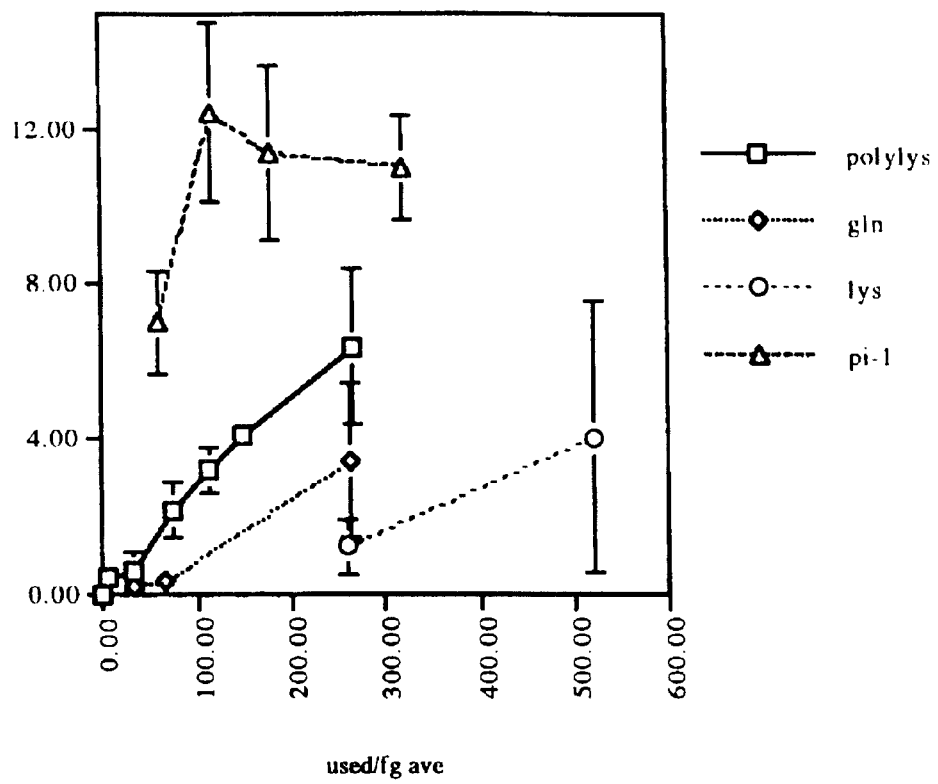
FIG. 3. Each curve represents the different crosslinking abilities of the four peptides. The molar excess of peptide used is plotted against the ratio of peptide molecules to fibrinogen molecules for a series of peptide concentrations. Gln and Lys represent the two peptides that mimic the g-chain of fibrinogen. Polylys is the multiple lysine peptide and pi-1 is the sequence from α2-plasmin inhibitor --□-- poly lys=SEQ ID NO:10; --◊-- gln=SEQ ID NO:8; --o-- lys=SEQ ID NO:9; --Δ-- pi=1=SEQ ID NO:11.
Figure 4:
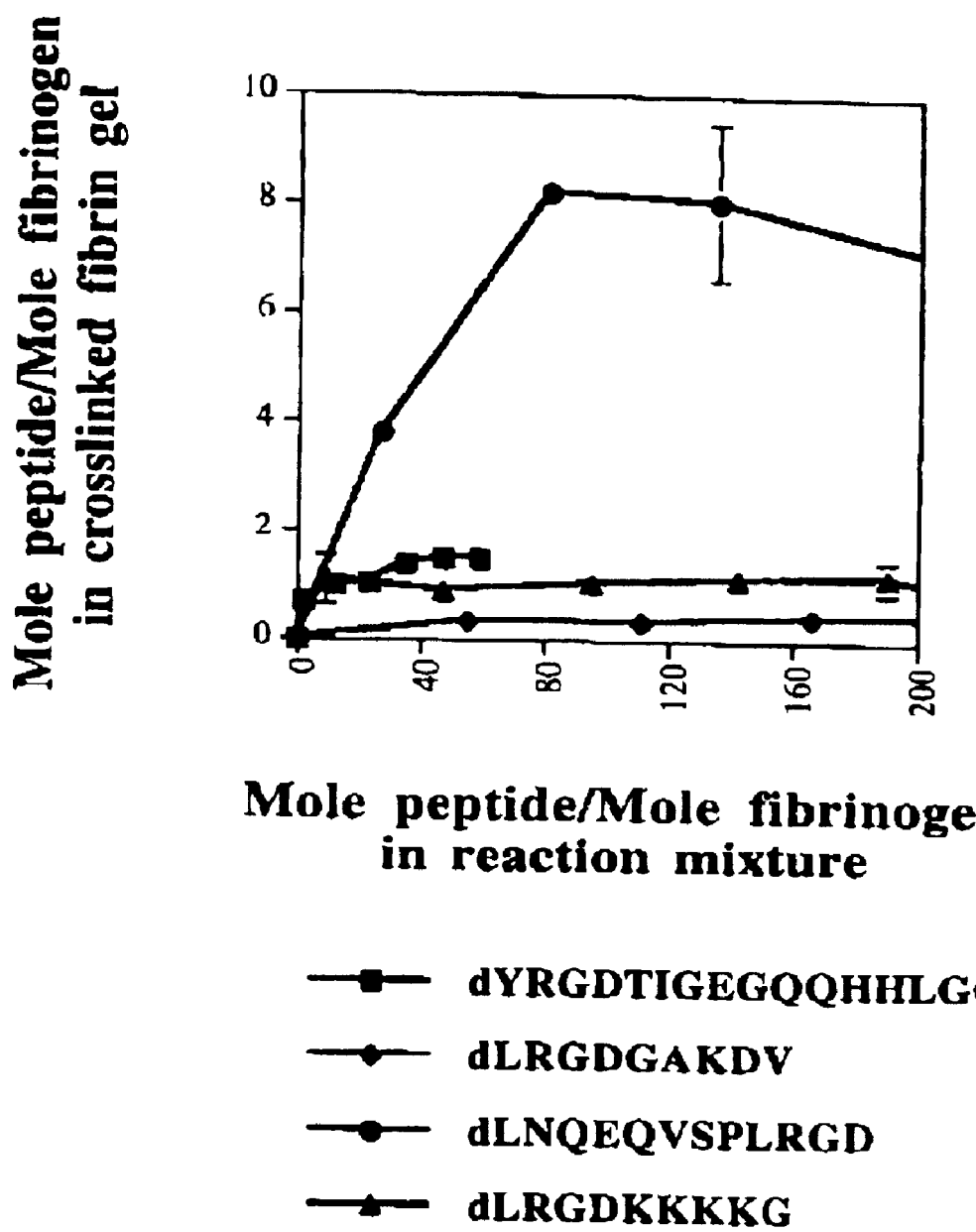
FIG. 4. Each curve represents the different crosslinking abilities of the four peptides. The molar ratio of peptide to fibrinogen in the initial reaction mixture is varied and plotted on the x axis. The ratio of crosslinked peptide to fibrinogen is then measured and plotted on the y axis --■-- dYRGDT1GEGQQHHLGG=SEQ ID NO:8; --♦-- dLRGDGAKDV=SEQ ID NO:9; --●-- dLNQEQVSPLRGD=SEQ ID NO:11; --▲-- dLRGDKKKKG=SEQ ID NO:10.

By washing peptide decorated gels, degrading them with plasmin and performing size exclusion chromatography, the amount of peptide bound per molecule of fibrinogen was calculated for a series of peptide concentrations and for four separate peptide sequences. All the substrate sequences tested included RGD as an exemplary bioactive sequence. The sequences tested include two that mimic the crosslinking site in the δ chain of fibrinogen, *YRGDTIGEGQQHHLGG (SEQ ID NO: 8) (* indicates the dansyl group and the section in italics is the native sequence of the crosslinking region of fibrinogen), a peptide with glutamine at the transglutaminase coupling site, and *LRGDGAKDV (SEQ ID NO: 9), a mimic of the lysine coupling site. Additionally a peptide with a polylysine at a random coupling site, *LRGDKKKKG (SEQ ID NO: 10), and a sequence that mimics the crosslinking site in α2-plasmin inhibitor, *LNQEQVSPLRGD (SEQ ID NO: 11) were also used. The amount of peptide covalently bound to the fibrin gels was measured while varying the initial excess of peptide for each of the four sequences. A concentration dependent curve was created (FIG. 3) and the maximum crosslinking ratio and the molar excess needed to achieve a 1:1 ratio are shown below in Table 1. Since a particular active sequence is usually present once in each protein, the excess of peptide required to achieve this concentration provides an interesting benchmark. The peptide that provides the greatest possible crosslinking concentration will provide the most flexibility. From the results seen in FIG. 4, the plasmin inhibitor peptide is the best, since it provides the highest crosslinking concentration and the greatest crosslinking efficiency.

TABLE 1

| Peptide Sequence | Maximum Crosslinking Ratio Pep/Fibrinogen | Molar excess needed to achieve 1:1 ratio |
|---|---|---|
| *YRGDTIGEGQQHHLGG SEQ ID NO: 8 | 1.53 | 12 |
| *LRGDGAKDV SEQ ID NO: 9 | 0.44 | >330 |
| *LRGDKKKKG SEQ ID NO: 10 | 1.2 | 11 |
| *LNQEQVSPLRGD SEQ ID NO: 11 | 8.2 | 6 |

This table shows the amount of peptide needed to covalently bind one peptide molecule per fibrinogen molecule in a fibrin gel.

Figure 5:
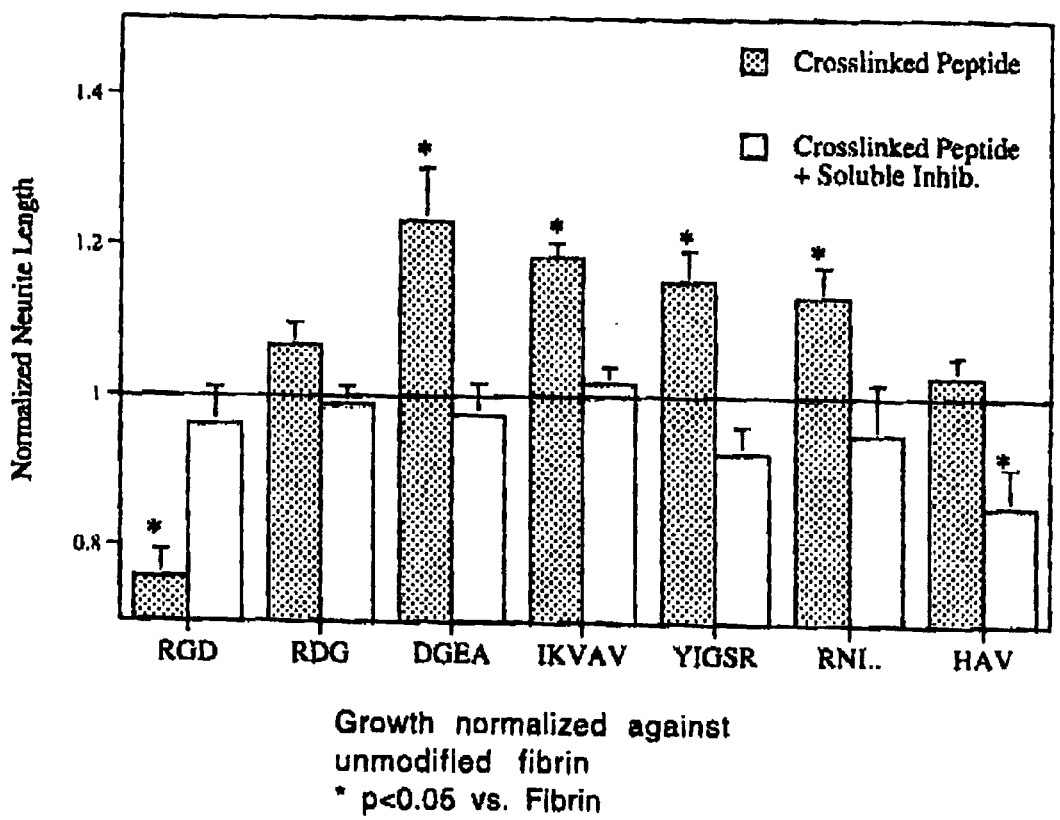
FIG. 5. Growth normalized against unmodified fibrin IKVAV (SEQ ID NO:4); RNIAEIIKDI (SEQ ID NO:1); YIGSR (SEQ ID NO:1); and RGR.

A collection of peptides utilizing the crosslinking sequence from α2-plasmin inhibitor have been made using active peptide sequences from the basement membrane molecules laminin and collagen SEQ ID NO: 11, and 16–20). Eight day chicken dorsal root ganglia were polymerized inside gels that had enough peptide to achieve the highest crosslinked concentration possible (8 moles peptide/mole fibrinogen). The extension of neurites from the ganglia was measured at 24 and 48 hours. The 48 hour data is shown in FIG. 5. The average neurite length for each experimental condition was normalized against growth in unmodified fibrin. Four of the active peptides used, IKVAV (SEQ ID NO: 4), RNIAEIIKDI (SEQ ID NO: 5), YIGSR (SEQ ID NO: 1) and RGD demonstrated statistically different neurine growth, proving that not only can different factors be attached to the fibrin gels, but they retain biologically significant activity. Soluble inhibitor experiments were completed as well, and in each trial, the neurite growth was statistically the same as unmodified fibrin. This result demonstrates that the activity is interrupted, then the presence of crosslinked peptide does not inhibit neural extension. The growth in RDG crosslinked fibrin also supports this conclusion, as the neurites are able to attain similar growth with this nonactive peptide presence as is achieved in unmodified fibrin.

EXAMPLE 2

The present example is provided to demonsrate the utility of the present invention for providing the covalent attachment of a bioactive factor to a peptide matrix, the amount of the bioactive factor, such as a peptide, being quantitatively determinable.

Using the spectrofluorimetry method (second method) described above, the amount of peptide bound per molecule of fibrinogen was calculated for a series of peptide concentrations and for four separate peptide sequences. The sequences tested include two that mimic the crosslinking site in the γ chain of fibrinogen, *YRGDTIGEGQQHHLGG (SEQ ID NO: 8) (* indicates the dansyl group and the section in italics is the native sequence of the crosslinking region of fibrinogen), a peptide with glutamine at the transglutaminase coupling site, and *LRGDGAKDV(SEQ ID NO: 9), a mimic of the lysine coupling site. Additionally a peptide with a polylysine at a random coupling site, *LRGDKKKKG (SEQ ID NO: 10), and a sequence that mimics the crosslinking site in α2-plasmin inhibitor, *LNQEQVSPLRGD (SEQ ID NO: 11) were also tested. The coupling of each peptide used was measured by determining the excess moles of peptide needed to get one peptide covalently bound to each fibrinogen molecule present. Since a particular active sequence is usually present once in each protein, this is a suitable benchmark. From the results seen in FIG. 3, it is clear that the plasmin inhibitor peptide (pi-1) is the best, the peptide with the sequence of multiple lysines (polylys) has the second highest coupling rate, while the two γ chain peptides (gln and lys) follow. The actual amount of peptide needed to achieve a 1:1 ratio of peptide to fibrinogen is shown in Table 2.

TABLE 2

| Peptide sequence | Molar excess needed to achieve 1:1 ratio |
| --- | --- |
| *YRGDTIGEGQQHHLGG SEQ ID NO: 8 | 110 |
| *LRGDGAKDV SEQ ID NO: 9 | 220 |
| LRGDKKKKG SEQ ID NO: 10 | 39 |
| *LNQEQVSPLRGD SEQ ID NO: 11 | ~10 |

Table 2 shows the amount of peptide needed to covalently bind one peptide molecule per fibrinogen molecule in a fibrin gel.

A Factor XIIIa substrate has been synthetically coupled to a bioactive peptide sought for incorporation into the fibrin matrix, and it is clear that this bioactive factor need not have been a peptide. While not intending to be limited to any particular mechanism of action or theory of operation, any bioactive or biologically or medically useful molecule or macromolecule could be the bioactive factor. Likewise, the coupling between the bioactive factor and the transglutaminase substrate domain could have been performed by recombinant DNA methodology or any other means. For example, a protein growth factor could be incorporated by recombinantly expressing a fusion protein comprising both a transglutaminase substrate domain and the growth factor domain. Furthermore, the transglutaminase substrate domain could be targeted for a translutaminase other than factor XIIIa. Furthermore, a recombinant form of fibrinogen could be used to form the fibrin network. Furthermore, other proteins that transglutaminase recognizes, such as fibronectin for example, could be coupled to the transglutaminase substrate peptide.

There are numerous applications for these fibrin gels that are derivitized with a bioactive factor. Fibrin is a natural matrix found in the body and is utilized in many ways. Although fibrin does provide a solid support for tissue regeneration and cell ingrowth, there are few active sequences in the monomer that directly enhance these processes. However, other studies have shown that many proteins, including basement membrane proteins such as laminin and growth factors such as basic fibroblast growth factor, have sequences which directly enhance regeneration or migration. Our method allows us to incorporate an active sequence or entire factor into the gels and create gels which possess specific bioactive properties.

The present invention provides the first description of a means by which to effectively incorporate bioactive factors into fibrin, a therapeutically important material in wound healing and tissue engineering have been provided. Hence a previously unaccomplished goal is presented that provides an important therapeutic material.

EXAMPLE 3

Bioactivity In Situ Ganglia Model

Bioactivity can be quantified using cell studies based on the 8-day chicken dorsal root ganglia model. With this model, addition of neuronally active sequences to the peptide can be tested for their ability in vitro to enhance neurite extension. Ganglia were dissected from eight day old chicken embryos and fibrin gels were polymerized around them. Peptide with different active sequences was crosslinked into these gels and the unbound peptide was washed out by periodically changing the neuronal media on top of the gels. These ganglia then extend neurites in three dimensions and the projection of these neurites can be captured using imaging software. This image can then be used to calculate the average neurite length. Three control experiments were done. Neurites were grown in fibrin gels without any peptide crosslinked, in fibrin gels with a non-active peptide crosslinked in and in gels with active peptide crosslinked and soluble peptide present in the media as an inhibitor.

EXAMPLE 4

Nerve Regeneration and Scaffold

The present example demonstrates the utility of the present invention as a tissue regenerational supportive material. In addition, the data here demonstrates the utility of the invention for supporting the effective regeneration of nerve tissue.

A collection of peptides utilizing the crosslinking sequence from α2-plasmin inhibitor have been made using active peptide sequences from the basement membrane molecules laminin and collagen. Eight day chicken dorsal root ganglia were polymerized inside gels that had enough peptide to achieve the highest crosslinked concentration possible (8 moles peptide/mole fibrinogen). The extension of neurites from the ganglia was measured at 24 and 48 hours. the 48 hour data is shown in FIG. 5. The average neurite length for each experimental condition was normalized against growth in unmodified fibrin. Four of the active peptides used, IKVAV (SEQ ID NO: 4), RNIAEIIKDI (SEQ ID NO: 5), YIGSR (SEQ ID NO: 1) and RGD, demonstrated statistically different neurite growth, proving that not only can different factors be attached to the fibrin gels, but they retain biologically significant activity. Soluble inhibitor experiments were completed as well, and in each trial, the neurite growth was statistically the same as unmodified fibrin. This result demonstrates that the activity of each sequence added is dependant on the physical crosslinking. Furthermore, this shows that if the neuronal activity of the attached factor is interrupted, then the presence of crosslinked peptide does not inhibit neural extension. The growth in RDG crosslinked fibrin also supports this conclusion, as the neurites are able to attain similar growth with this nonactive peptide present as is achieved in unmodified fibrin.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references are specifically incorporated herein by reference for the various purposes described herein.

1. Sierra, D. H. "Fibrin Sealant Adhesive Systems, A Review of Their Chemistry, Material Properties and Clinical Applications"; *Journal of Biomaterials Applications* 7:309–352, 1993.
2. Williams, et al., "Exogenous fibrin matrix precursors promote functional nerve regeneration across a 15-mm gap within a silicone chamber in a rat."; *Journal of Comparative Neurobiology,* 264:284–290, 1987.
3. Francis, et al., "Endothelial Cell Responses to Fibrin Mediated by FPB Cleavage and the Amino Terminus of the B Chain"; *Blood Cells,* 19:291–307, 1993.
4. Stryer, L. in *Biochemistry* 233–260 (W. H. Freeman and Company, New York, 1975).
5. Aoki, N. "Natural inhibitors of fibrinolysis."; *Progress in Cardiovascular Disease* 21:267–286, 1979.
6. Sakata, Y & N. Aoki, "Cross-Linking of α 2-Plasmin Inhibitor to Fibrin by Fibrin-stabilizing Factor," *Journal of Clinical Investigation,* 65:290–297, 1980.
7. Aoki, et al., "Effects of α2-plasmin inhibitor on fibrin clot lysis. Its comparison with α2-macroglobulin,." *Thrombosis and Haemostasis,* 39:22–31, 1978.
8. Carey, D. J., "Control of growth and differentiation of vascular cells by extracellular matrix research," *Annual Review of Physiology,* 53:161–177, 1991.
9. Lander, A., "Understanding the molecules of cell contacts," *Journal of Trends in Neurological Science,* 12:189–195, 1989.
10. Williams, L. R., "Exogenous fibrin matrix precursors stimulate the temporal progress of nerve regeneration within a silicone chamber," *Neurochemical Research,* 12: 851–860, 1987.
11. Martin, G. R., "Laminin and other basement membrane proteins," *Annual Review of Cellular Biology,* 3:57–85, 1987.
12. Graf, et al., "Identification of an Amino Acid Sequence in Laminin Mediating Cell Attachment, Chemotaxis, and Receptor Binding," *Cell,* 48:989–996, 1987.
13. Kleinman, et al., "Identification of a second site in laminin for promotion of cell adhesion and migration and inhibition of in vivo melanoma lung colonization," *Archives of Biochemistry and Biophysics,* 272:39–45, 1989.
14. Massia, et al., "Covalently immobilized laminin peptide tyr-ile-gly-ser-arg (YIGSR) supports cell spreading and colocalization of the 67 kilodalton receptor with α-actinin and viniculin," *Journal of Biological Chemistry,* 268:8053–8059, 1993.
15. Ignatius, et al., "Lipoprotein uptake by neuronal growth cones in vitro," *Journal of Cell Biology,* 111:709–720, 1990.
16. Tashiro, et al,. "The RGD containing site of mouse laminin A chain is active for cell attachment," *Journal of Biological Chemistry,* 264:16174–16182, 1989.
17. Liesi, et al., "Identification of a neurite-outgrowth promoting domain using synthetic peptides," *FEBS letters,* 244:141–148, 1989.
18. Rouslahti, E., "Integrins," *Journal of Clinical Investigation,* 87:1–5, 1991.
19. Hynes, R. O., "Integrins: Versatility, Modulation, and Signaling in Cell Adhesion," *Cell,* 69:1–25, 1992.
20. Yamada, K. M., "Adhesive Recognition Sequences," *Journal of Biological Chemistry,* 266:12809–12812, 1991.
21. Tashiro, et al., "A synthetic peptide containing the IKVAV sequence from a chain of laminin mediates cell attachment, migration and neurite outgrowth," *Journal of Biological Chemistry,* 264:16174–16182, 1989.
22. Luckenbill-Edds, et al., "Localization of the 110 dKa receptor for laminin in brains of embryonic and postnatal mice," *Cell Tissue Research,* 279:371–377, 1995.
23. Zutter, M. M. & S. A. Santaro, "Widespread histologic distribution of the $\alpha_2\beta_1$ integrin cell-surface receptor," *American Journal of Pathology,* 137:113–120, 1990.
24. Herbert, C. in *Chemical Engineering* 146 (University of Texas, Austin, Austin 1996).
25. Doolittle, et al., "Hybrid fibrin: Proof of the intermolecular nature of γ-γ crosslinking units," *Biochemical and Biophysical Research Communications,* 44: 94–100, 1971.
26. Barry, E. & D. Mosher, "Factor XIIIa-mediated Cross-linking of Fibronectin in Fibroblast Cell Layers," *Journal of Biological Chemistry,* 264:4179–4185, 1989.
27. Okada, et al., "Fibronectin and fibrin gel structure," *Journal of Biological Chemistry,* 260:1811–1820, 1985.
28. Hada, et al., "Covalent crosslinking of von Willebrand factor to fibrin," *Blood,* 68:95–101, 1986.
29. Tamaki, T. & N. Aoki, "Cross-linking of α2-Plasmin Inhibitor to Fibrin Catalyzed by Activated Fibrin-stabilizing Factor," *Journal of Biological Chemistry,* 257:14767–14772, 1982.
30. Ichinose, et al., "Factor XIII-mediated cross-linking of NH2-terminal peptide of α2-plasmin inhibitor to fibrin," *FEBS Letters,* 153:369–371, 1983.
31. Sobel, J. & M. Gawinowicz, "Identification of the alpha chain lysine donor sites involved in factor XIIIa fibrin crosslinking," *Journal of Biological Chemistry,* 271:19288–19297, 1996.

What is claimed is:

1. An implantable device having at least one surface comprising a composition, wherein the composition comprises a fibrin network and a non-fibrin peptide, wherein the peptide is not fibrin or a fragment thereof, the peptide having an amino acid sequence that comprises one transglutaminase substrate domain and a bioactive domain, wherein the peptide is covalently bound to the fibrin network by the transglutaminase substrate domain.

2. The implantable device of claim 1 further defined as an artificial joint device.

3. A porous vascular graft comprising in at least one region of a porous wall of the porous vascular graft a composition, wherein the composition comprises a fibrin network and a non-fibrin peptide, wherein the peptide is not fibrin or a fragment thereof, the peptide having an amino acid sequence that comprises one transglutaminase substrate domain and a bioactive domain, wherein the peptide is covalently bound to the fibrin network by the transglutaminase substrate domain.

4. A scaffold for cell growth comprising a surface that comprises at least one region that includes a composition comprising a fibrin network and a non-fibrin peptide having an amino acid sequence that comprises one transglutaminase substrate domain and a bioactive domain, wherein the peptide is covalently bound to the fibrin network by the transglutaminase substrate domain.

5. The scaffold of claim 4 wherein the cell growth is bone cell growth, skin cell growth, or nerve cell growth.

6. The scaffold of claim 4 further defined as a scaffold for nerve cell growth.

7. A surgical adhesive or sealant comprising a surface that includes at least one region of a composition comprising a fibrin network and a non-fibrin peptide having an amino acid sequence that comprises one transglutaminase substrate domain and a bioactive domain, wherein the peptide is covalently bound to the fibrin network by the transglutaminase substrate domain.

8. A biosupportive matrix material comprising a fibrin network and a non-fibrin peptide having an amino acid sequence that contains one transglutaminase substrate domain and a bioactive domain, wherein the peptide is covalently attached to the fibrin network by the transglutaminase substrate domain.

9. The biosupportive matrix material of claim 8 wherein the bioactive factor is covalently attached to the fibrin network through a transglutaminase.

10. The biosupportive matrix material of claim 8 wherein the peptide has an amino acid sequence of SEQ ID NO: 1, SEQ ID NO: 4, SEQ ID NO: 5, SEQ ID NO: 10, a combination thereof, or a bioactive fragment thereof.

11. The biosupportive matrix material of claim 8 wherein the peptide has an amino acid sequence of SEQ ID NO: 10.

12. The implantable device of claim 1 wherein the transglutaminase substrate domain is a factor XIIIa substrate domain.

13. The implantable device of claim 12 wherein the factor XIIIa substrate domain comprises an amino acid sequence of SEQ ID NO: 12, SEQ ID NO: 13, SEQ ID NO: 14, SEQ ID NO: 15, a fragment thereof, a combination thereof, or a bioactive fragment thereof.

14. The implantable device of claim 13 wherein the factor XIIIa substrate domain comprises an amino acid sequence of SEQ ID NO: 15.

15. The implantable device of claim 1 wherein the bioactive domain is a peptide.

16. The implantable device of claim 1 wherein the bioactive domain comprises an amino acid sequence of SEQ ID NO: 1, SEQ ID NO: 2, SEQ ID NO: 3, SEQ ID NO: 4, SEQ ID NO: 5, SEQ ID NO: 6, a combination thereof, or a bioactive fragment thereof.

17. The implantable device of claim 12 wherein the bioactive domain is a protein.

18. The implantable device of claim 17 wherein the bioactive factor is a polypeptide growth factor.

19. The porous vascular graft of claim 3 wherein the transglutaminase substrate domain is a factor XIIIa substrate domain.

20. The porous vascular graft of claim 19 wherein the factor XIIIa substrate domain comprises an amino acid sequence SEQ ID NO: 12, SEQ ID NO: 13, SEQ ID NO: 14, SEQ ID NO: 15, a fragment thereof, a combination thereof, or a bioactive fragment thereof.

21. The porous vascular graft of claim 19 wherein the factor XIIIa substrate domain comprises an amino acid sequence of SEQ ID NO: 15.

22. The porous vascular graft of claim 3 wherein the bioactive domain is a peptide.

23. The porous vascular graft of of claim 2 wherein the bioactive domain comprises an amino acid sequence of SEQ ID NO: 1, SEQ ID NO: 2, SEQ ID NO: 3, SEQ ID NO: 4, SEQ ID NO: 5, SEQ ID NO: 6, a combination thereof, or a bioactive fragment thereof.

24. The porous vascular graft of claim 19 wherein the bioactive domain is a protein.

25. The porous vascular graft of claim 24 where the bioactive domain is a polypeptide growth factor.

26. The scaffold of claim 4 wherein the transglutaminase substrate domain is a factor XIIIa substrate domain.

27. The scaffold of claim 26 wherein the factor XIIIa substrate domain comprises an amino acid sequence SEQ ID NO: 12, SEQ ID NO: 13, SEQ ID NO: 14, SEQ ID NO: 15, a fragment thereof, a combination thereof or a bioactive fragment thereof.

28. The scaffold of claim 27 wherein the factor XIIIa substrate comprises an amino acid sequence of SEQ ID NO: 15.

29. The scaffold of claim 4 wherein the bioactive domain is a peptide.

30. The scaffold of claim 4 wherein the bioactive domain comprises an amino acid sequence of SEQ ID NO: 1, SEQ ID NO: 2, SEQ ID NO: 3, SEQ ID NO: 4, SEQ ID NO: 5, SEQ ID NO: 6, a combination thereof, or a bioactive fragment thereof.

31. The scaffold of claim 4 wherein the bioactive domain is a protein.

32. The scaffold of claim 31 where the bioactive domain is a polypeptide growth factor.

33. The surgical adhesive or sealant of claim 7 wherein the transglutaminase substrate domain is a factor XIIIa substrate domain.

34. The surgical adhesive or sealant of claim 7 wherein the transglutaminase substrate domain comprises an amino acid sequence SEQ ID NO: 12, SEQ ID NO: 13, SEQ ID NO: 14, SEQ ID NO: 15, a combination thereof, or a bioactive fragment thereof.

35. The surgical adhesive or sealant of claim 33 wherein the factor XIIIa substrate domain comprises an amino acid sequence of SEQ ID NO: 15.

36. The surgical adhesive or sealant of claim 7 wherein the bioactive domain is a peptide.

37. The scaffold of claim 26 wherein the bioactive domain comprises an amino acid sequence of SEQ ID NO: 1, SEQ ID NO: 2, SEQ ID NO: 3, SEQ ID NO: 4, SEQ ID NO: 5, SEQ ID NO: 6, a combination thereof, or a bioactive fragment thereof.

38. The scaffold of claim 26 wherein the bioactive domain is a protein.

39. The scaffold of claim 38 wherein the bioactive domain is a growth factor.

* * * * *

UNITED STATES PATENT AND TRADEMARK OFFICE
CERTIFICATE OF CORRECTION

PATENT NO. : 6,331,422 B1
APPLICATION NO. : 09/057052
DATED : December 18, 2001
INVENTOR(S) : Jeffery A. Hubbell and Jason Schense It is certified that error appears in the above-identified patent and that said Letters Patent is hereby corrected as shown below:

On Title Page Item (22) Filed:   Apr. 8, 1998", insert -- Related U.S. Application Data Continuation of PCT/US98/06617, filed on April 2, 1998, which claims priority to Provisional application No. 60/042,143 filed on April 3, 1997.--

Signed and Sealed this

Thirty-first Day of October, 2006

JON W. DUDAS
*Director of the United States Patent and Trademark Office*